United States Patent [19]

Cooper

[11] 4,405,212

[45] Sep. 20, 1983

[54] SPECTACLE FRAME AND CONVERSION ACCESSORIES THEREFOR

[76] Inventor: Leonard B. Cooper, Capri G300, Delray Beach, Fla. 33446

[21] Appl. No.: 213,949

[22] Filed: Dec. 8, 1980

Related U.S. Application Data

[63] Continuation-in-part of Ser. No. 107,322, Dec. 26, 1979, abandoned.

[51] Int. Cl.³ .................................................. G02C 5/00
[52] U.S. Cl. .................................... 351/43; 2/440; 351/41; 351/83; 351/158
[58] Field of Search .................. 351/43, 83, 116, 158, 351/41, 44–49, 154, 156; 2/426, 439, 440, 441–443, 445–448, 450, 452

[56] References Cited

U.S. PATENT DOCUMENTS 2,393,533  1/1946  Heinz ...................................... 2/440
4,256,386  3/1981  Herbert ................................. 351/43

OTHER PUBLICATIONS

Mechanix Illustrated, Jun. 1959, p. 61.

*Primary Examiner*—F. L. Evans
*Attorney, Agent, or Firm*—Evans Kahn

[57] ABSTRACT

The invention provides a spectacle frame having on its inner (rear) face a circumferential channel, and frame-to-face seals carrying a mating ridge on the outer (forward) face of each seal. The spectacle frame is converted to an air-vented safety goggle, to a watertight swimmer's goggle or to an underwater diving mask by mating the appropriate frame-to-face seal with the channel in the frame; the frame can carry plano or prescription ground lenses and may be provided with temples or with an elastic headband.

6 Claims, 8 Drawing Figures

SPECTACLE FRAME AND CONVERSION ACCESSORIES THEREFOR

This is a continuation-in-part of my copending application Ser. No. 107,322 filed on Dec. 26, 1979 now abandoned.

The present invention relates to a spectacle frame which when provided with appropriate accessories is adapted to be worn as an every-day spectacle, as a safety goggle, as a watertight swimming goggle, and as an underwater diver's mask. The invention includes the spectacle frame itself, the accessories, and the frame in various combinations with the accessories.

BACKGROUND OF THE INVENTION

The optical art has provided many varieties of spectacles of the every-day type (for reading or distant viewing), industrial safety eyewear, soft plastic safety goggles (for use with power tools), ski and motorcycle goggles, swimming and underwater diving goggles. The every-day type of spectacle is designed to provide the wearer with corrective lenses for his eyes and usually the spectacle is not worn to obtain the protection provided by the other types of eyewear mentioned. The corrective spectacles and the types of goggles mentioned have developed largely independently, and at the present time a person desiring a corrective spectacle, a corrective safety goggle and corrective swimming and diving goggles has little choice but to purchase each type separately. Safety goggles, ski and motorcycle goggles may be purchased to fit over a small-size spectacle frame, but this is a bulky arrangement and it is uncomfortable to wear two eyepieces at the same time. It is not practical or even possible to wear every-day spectacles under swimming and diving goggles as the temples of the spectacles would break the watertight seal between the goggles and the face.

The aforesaid difficulties are substantially obviated by the present invention, which provides a spectacle frame which is apparently of the every-day type but which readily receives accessories which convert it into a safety goggle of the types mentioned, and also receives accessories which convert it to swimming and underwater diving goggles. The frame may carry optically neutral (plano) lenses which can be fitted when the frame is manufactured and which are used when the vision of the wearer does not require correction, or the frame can be supplied without lenses permitting prescription ground lenses to be fitted by others when the frame is sold to the ultimate user. The frame may be attached to the head by temples or by a headband, as may be most comfortable or required in any instance. When supplied with plano lenses the frame can receive 6-base ground and polished lenses which are optically superior to the flexible plastic "windows" provided by most goggles. The invention thus provides a person with normal vision with a spectacle which, after attachment of appropriate accessories, can be used for many mutually exclusive purposes without any distortion to his good vision and which provides a person with defective vision with an every-day spectacle having prescription ground lenses which can be converted to protective eyewear for shop safety, sport (motorcycling, skiing etc.) which meets health requirements (dry eye etc.), to a swimming goggle or to an underwater mask as may be desired.

More in detail, the invention provides a spectacle frame which has in its inner face a substantially circumferential channel adapted to retain with a tight fit a correspondingly ridged frame-to-face sealing component (hereinafter termed "seal"). The channel can be undercut to provide a tighter grip on the ridge, and at one or more places on its inner (rear) face the frame may have one or more holes or indentations to receive correspondingly positioned plugs in the ridge surface of the seal to facilitate positioning of the ridge of the seal with the channel of the frame, and to improve retention of the seal by the frame. Each side of the frame may carry a means for the attachment of a temple or a headband, each interchangable with the the other. The frame itself may have a wrap-around configuration to facilitate the receiving of the seals and to provide a wider arc of vision.

The invention further provides, as one of the aforementioned accessories, a frame-to-face seal for converting the frame into a goggle. The forward side of the seal is substantially flat and carries a circumferential retaining ridge which is adapted to mate with a corresponding circumferential channel in the rear side of the frame so as to engage the channel with a friction fit. The rear side of the seal is contoured to fit the face of the wearer closely. To convert the frame to a safety goggle the seal is inserted into the frame providing the wearer with eye protection around the outer sides, top and bottom of his eyes. An air space is provided between the eye cups to permit a stream of air to flow along the sides of the nose and through the nose bridge of the wearer in an amount which is necessary to prevent fogging of the lenses but which is not sufficient to cause drying of the eyes. The seals which convert the spectacle frame to a swimming goggle and to an underwater diving mask are of the single circumferential type that forms a watertight seal with the wearer's face, leaving the nose free to breathe in the swimming goggle, and completely sealing the nose in the diving mask. The watertight seal in the swimming goggle is attained with a face-formed flexible rubber or rubber-like skirt, or by the use of a continuous band of compressible foam rubber. The diving mask is constructed of a formed sheet of rubber or rubber-like material that provides a watertight fit around the eyes and nose of the wearer.

When used as an every-day spectacle and when used as a safety goggle, the frame is normally provided with temples which are preferably detachable. When the mask is used for swimming and diving, a headband must be attached either to the temple ends or to the frame replacing the temples, so that a watertight seal can be maintained.

The invention is further described in the drawings, wherein.

In the figures, the same components are designated by the same numerals.

Figure 1:
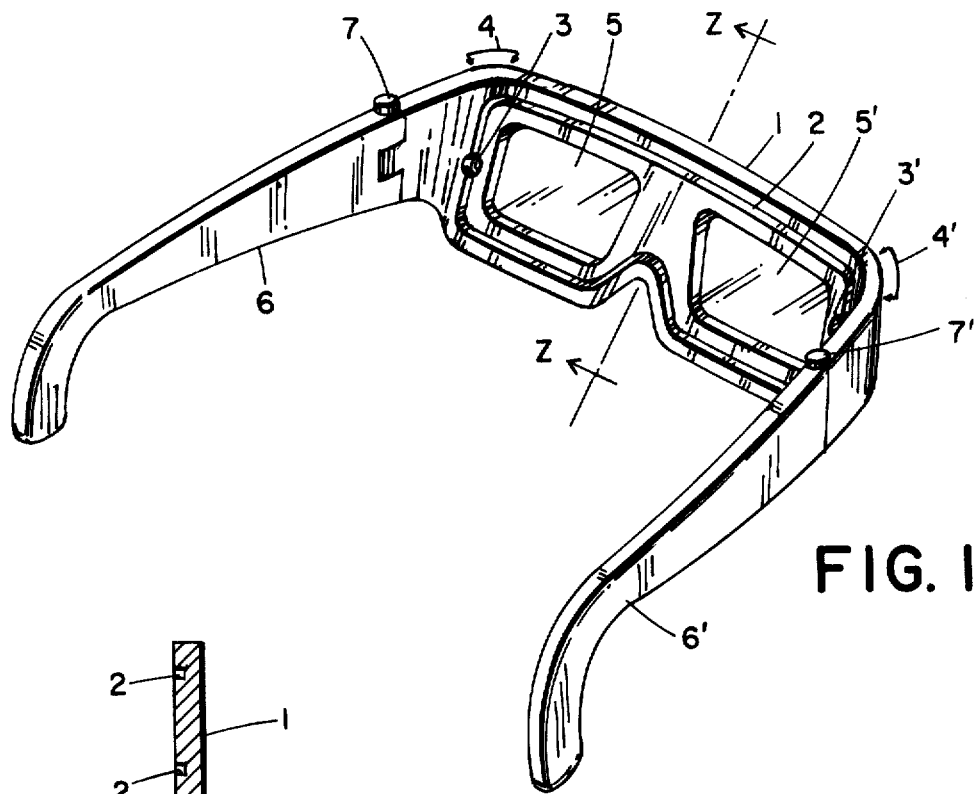
FIG. 1 is a view from the above rear of a spectacle frame according to the invention fitted with lenses and temples.
Figure 2:
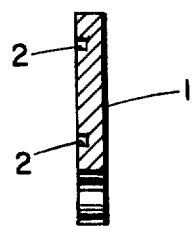
FIG. 2 is a vertical section of the spectacle frame of FIG. 1 taken along line Z—Z thereof.

In FIGS. 1 and 2, a spectacle of the present invention is shown as comprising molded spectacle frame 1 having circumferential channel 2 and optional postholes 3 and 3' molded into the rear face of frame 1. Frame 1 optionally is widened and curved at each of its sides to provide wrap-around curves 4 and 4', and optionally non-correcting or optionally correcting prescription-ground lenses 5, 5' are fitted into the lens openings of the frame by the same technique by which lenses are fitted into ordinary spectacles (the lens openings are expanded with mild heat enabling the lens to be inserted in a matching vee groove in the opening) but in a water-tight manner. Frame 1 carries removable temples 6 and 6' attached to frame 1 by removable threaded pins 7 and 7' (see FIG. 8).

Figure 3:
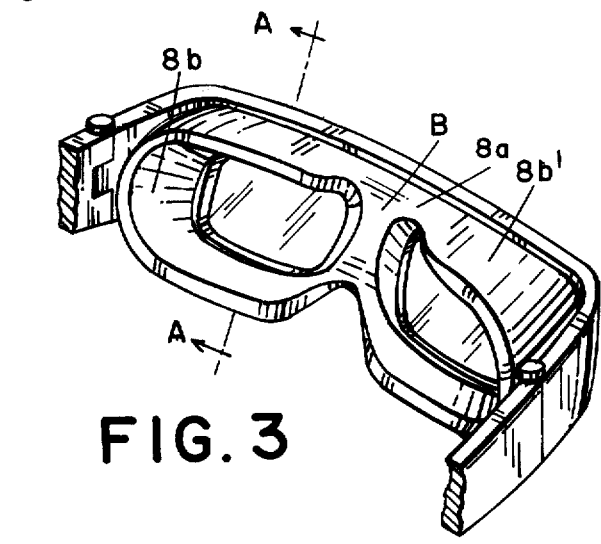
FIG. 3 is a view of the air-vented frame-to-face seal of the present invention for conversion of the spectacle of FIG. 1 into a safety, ski or motorcycle goggle.

In FIG. 3 is shown an inside view of the air-vented frame-to-face seal inserted in frame 1 converting the spectacles of FIG. 1 into a safety goggle. The two (right and left) foam eye cups 8b and 8b' are attached to base 8a, which consists of molded plastic, with an appropriate adhesive cement. Space B is provided between the eyecups to permit ventilation around the nose and nose bridge area.

Figure 4:
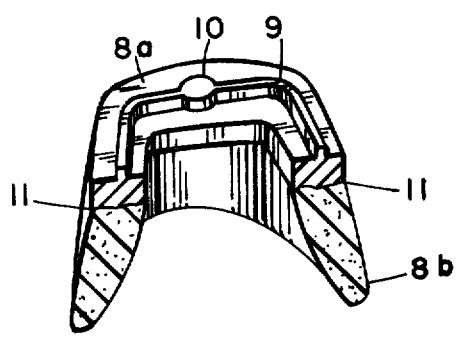
FIG. 4 is a view, partly in section, of the frame-to-face seal of FIG. 3 along line A—A of FIG. 3, showing the top ridge and plug of said seal.

In FIG. 4 base 8a is shown with retention ridge 9 and retention plug 10 that fit respectively into channel 2 and hole 3 of frame 1 in FIG. 1. Base 8a is joined by cement to foam eye cup 8b at junction line 11. Eye cups 8b and 8b' are contoured to fit snugly to the face of the wearer.

Figure 5:
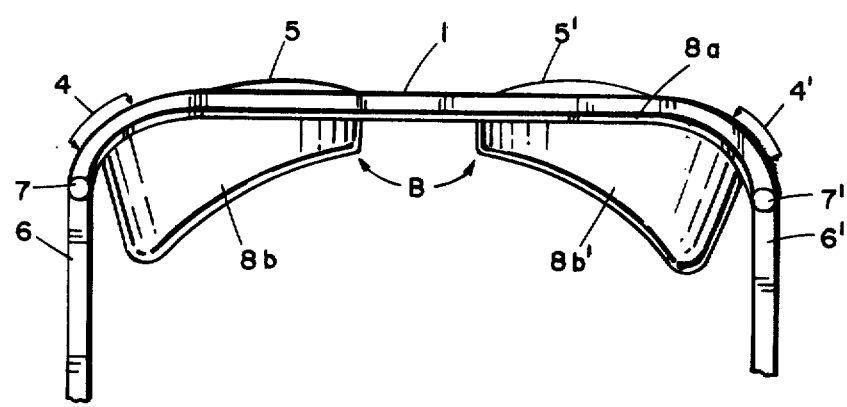
FIG. 5 is a view of the goggle of FIG. 3 as seen from above.

FIG. 5 shows a safety goggle comprising frame 1 mated with an air-vented frame-to-face seal consisting of base 8a, eye cups 8b, 8b', temples 6, 6', removable threaded pins 7, 7', lenses 5, 5', wrap-around curvature 4, 4', and space B that permits air ventilation of the goggle to prevent heat build-up and fogging.

Figure 6:
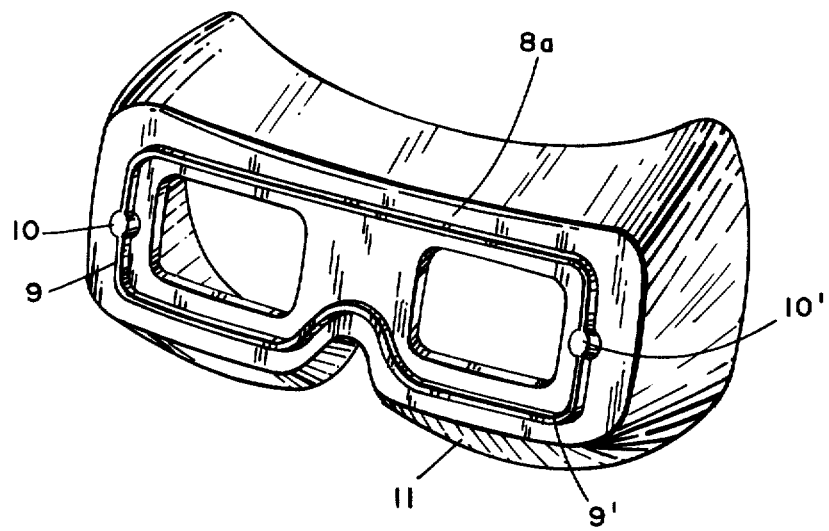
FIG. 6 is a view from the front of a frame-to-face seal for converting the spectacle of FIG. 1 to a swimming goggle.

In FIG. 6 is shown a frame-to-face seal adapted to convert the spectacle of FIG. 1 into a watertight swimming goggle. Base 8a retaining ridge 9 and retaining plugs 10 and 10' are molded as one piece with skirt 11 of flexible neoprene or other suitable material to form a watertight seal with the face of the wearer.

Figure 7:
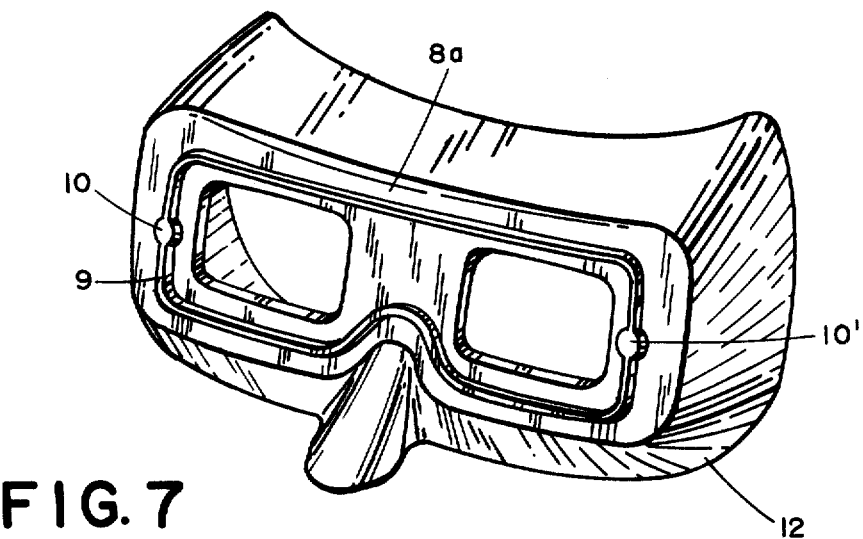
FIG. 7 is a view from the front of a frame to face seal for converting the spectacle of FIG. 1 to an underwater diving mask wherein the nose is completely sealed.

FIG. 7 shows a similar watertight frame-to-face seal as shown in FIG. 6 with skirt 12 completely sealing the wearer's nose to make a seal suitable for use by snorkel and scuba divers.

Figure 8:
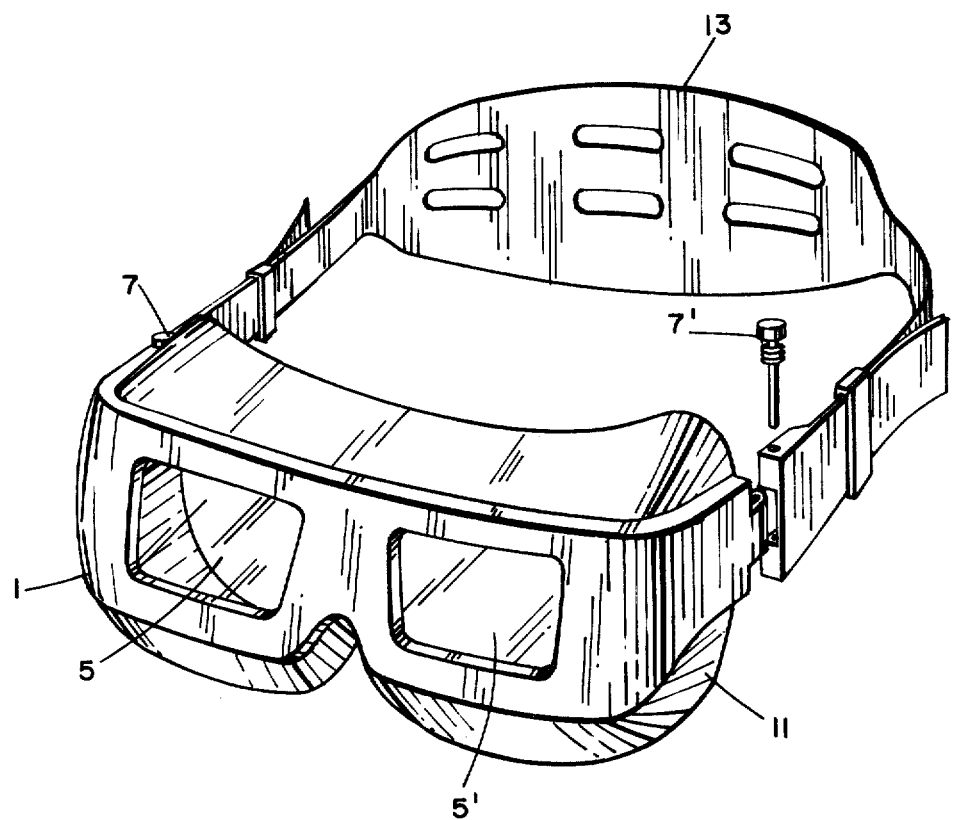
FIG. 8 is a view from the front above of the spectacle of FIG. 1 fitted with the frame-to-face seal of FIG. 6 and thereby converted to a swimming goggle with an adjustable headband in place of the temples.

FIG. 8 shows spectacle frame 1 fitted with the swimming goggle seal of FIG. 6 and adjustable headband 13, in place of temples, joined to the frame with threaded pins 7 and 7', which have large knurled heads for convenient manual removal. Lenses, 5, 5' are shown in place.

The components referred to above are constructed of materials such as are now used for the fabrication of every-day spectacles, safety goggles and underwater swimming and diving masks, and similar methods of fabrication are employed. Thus frame 1 and temples 6 and 6' can be formed by molding any of the optical thermo-plastic resins though nylon is preferred because of its strength. The preferred material for lenses 5, 5' is CR - 39 monomer, optical grade. Base 8a, with ridge 9 and retaining posts 10, 10' are preferably molded as an integral unit from a stiff but not rigid elastomeric thermoplastic material for example polyethylene, neoprene or silicon rubber. Eye cups 8b, 8b' are preferably constructed of soft, compressible foam which may be sheathed in a suitable material such as soft leather or vinyl, and the watermasks of FIGS. 6 and 7 are preferably molded of non-allergic neoprene. Headband 13 is preferably constructed of neoprene or other flexible waterproof material. The adhesive or adhesives used for cementing components together can be any adhesive which forms a strong water resistant flexible bond, and for this purpose emulsified poly(vinyl acetate) has been found generally satisfactory.

Obviously, modifications and variations of the present invention are possible in the light of the above teachings. It is therefore to be understood that any changes which may be made in the particular embodiments of the invention as are described above are within the full intended scope of the invention as defined by the appended claims.

I claim:

1. A spectacle frame of the every-day type convertible into a water-tight goggle, said frame having (1) manually detachable temples, (2) means for receiving a prescription ground lens in each eyepiece, and (3) in its inner face a circumferential channel adapted to hold with a tight fit a correspondingly ridged frame-to-face seal.

2. A spectacle frame according to claim 1 wherein said channel is undercut.

3. A spectacle frame according to claim 1 having at each temple end, in its inner face, a plughole adapted to hold a plug of elastomeric material in a tight friction fit.

4. A spectacle frame according to claim 1 wherein each side of said frame carries means for attachment of a head-band.

5. A spectacle frame according to claim 1 having a wraparound configuration.

6. An underwater swimmer's goggle comprising a spectacle frame having (1) a manually detachable headband connected to each side of said frame, (2) means for receiving a prescription ground lens in each eyepiece of said frame, (3) in its inner face a single circumferential channel adapted to hold with a water-tight fit a correspondingly ridged frame-to-face seal, and (4) a single circumferential frame-to-face water-impermeable seal for sealing said frame to the face of a wearer, the inner side of said seal being contoured to fit against the human face and the outer side of said seal being substantially flat and carrying a circumferential ridge, said ridge being mated into said channel with a snap fit.

* * * * *